United States Patent [19]

Costales et al.

[11] Patent Number: 5,447,905
[45] Date of Patent: Sep. 5, 1995

[54] N-INDAZOLYL[1,2,4]TRIAZOLO[1,5-C]PYRIMIDINE-2-SULFONAMIDE HERBICIDES

[75] Inventors: Mark J. Costales; Robert J. Ehr; William A. Kleschick; John C. Van Heertum, all of Indianapolis, Ind.; Walter Reifschneider, Walnut Creek, Calif.

[73] Assignee: DowElanco, Indianapolis, Ind.

[21] Appl. No.: 273,073

[22] Filed: Jul. 11, 1994

[51] Int. Cl.$^6$ .......................................... A01N 43/713
[52] U.S. Cl. ................... 504/241; 548/360.1; 544/263
[58] Field of Search .............. 544/263; 504/241; 548/360.1

[56] References Cited

U.S. PATENT DOCUMENTS

| | | | |
|---|---|---|---|
| 4,818,273 | 4/1989 | Kleschick et al. | 544/263 |
| 5,163,995 | 11/1992 | Van Heertum et al. | 544/263 |
| 5,177,206 | 1/1993 | Johnson et al. | 544/263 |
| 5,201,938 | 4/1993 | Costales et al. | 544/263 |
| 5,217,521 | 6/1993 | Durr | 544/263 |

FOREIGN PATENT DOCUMENTS 244948 11/1987 European Pat. Off. .
419831 8/1990 European Pat. Off. .

Primary Examiner—Donald G. Daus
Attorney, Agent, or Firm—D. Wendell Osborne

[57] ABSTRACT

Substituted N-indazolyl[1,2,4]triazolo[1,5]-c-pyrimidine-2-sulfonamide compounds, such as N-(4-fluoro-1-methyl-3-indazolyl)-5-ethoxy-7-fluoro[1,2,4]-triazolo[1,5-c]pyrimidine-2-sulfonamide, were prepared by condensation of a 2-chlorosulfonyl[1,2,4]-triazolo[1,5-c]pyrimidine compound, such as 2-chlorosulfonyl-5-ethoxy-7-fluoro[1,2,4]triazolo[1,5-c]pyrimidine, with a substituted 3-aminoindazole compound, such as 3-amino-4-fluoro-1-methylindazole, and found to possess herbicidal utility.

21 Claims, No Drawings

N-INDAZOLYL[1,2,4]TRIAZOLO[1,5-C]PYRIMIDINE-2-SULFONAMIDE HERBICIDES

BACKGROUND OF THE INVENTION

The present invention relates to substituted sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

A number of sulfonamide compounds, including certain substituted [1,2,4]triazolo[1,5-a]pyrimidine-2-sulfonamide compounds (U.S. Pat. No. 4,954,163) and [1,2,4]triazolo[1,5-c]pyrimidin-2-sulfonamide compounds (U.S. Pat. No. 5,010,195 and European Application 244,948), are known and are known to possess herbicidal activity, especially on broadleaf weeds.

SUMMARY OF THE INVENTION

It has now been found that certain N-indazolyl-[1,2,4]triazolo[1,5-c]pyrimidine-2-sulfonamide compounds are potent herbicides for the control of unwanted vegetation, have desirable crop selectivity, and have favorable toxicological and environmental attributes. The compounds can be used to control grassy as well as broadleaf weeds.

The invention includes N-indazolyl[1,2,4]-triazolo[1,5-c]pyrimidine-2-sulfonamide compounds of Formula I:

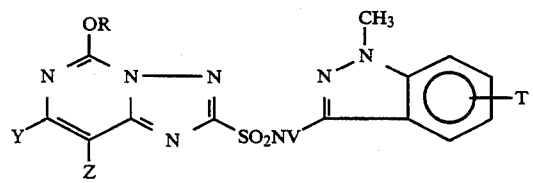

wherein
R represents $CH_2CF_3$ or $(C_1-C_3)$alkyl optionally monosubstituted with F, Cl, or $OCH_3$;
Y and Z each independently represents H, F, Cl, Br, I, $OCH_3$, $OC_2H_5$, or $CH_3$ optionally mono to completely substituted with F;
T represents H or F
V represents H, COR', $CO_2R''$, or $CONR'''_2$;
R' represents $(C_1-C_3)$alkyl optionally singly to completely substituted with fluorine;
R'' represents $(C_1-C_4)$alkyl, $(C_3-C_4)$alkenyl, or $(C_3-C_4)$alkynyl,
R''' represents H or $(C_1-C_4)$alkyl; and when V represents H, the agriculturally acceptable salts thereof.

The compounds of the invention, usually in the form of an herbicidal composition containing one or more of them in admixture with an agriculturally acceptable adjuvant or carrier, exhibit strong herbicidal properties when applied either directly to the unwanted vegetation or to the locus thereof and when applied either preemergence or postemergence.

DETAILED DESCRIPTION OF THE INVENTION

The N-indazolyl[1,2,4]triazolo[1,5-c]-pyrimidine-2-sulfonamide compounds of the invention can be characterized as [1,2,4]triazolo[1,5-c]pyrimidine-2-sulfonamide compounds possessing an alkoxy substituent in the 5-position, alkyl, substituted alkyl, alkoxy, or halogen substituents in either or both of the 7- and 8-positions, and a substituted 1-methyl-3-indazolyl moiety on the sulfonamide nitrogen atom. They are amides derived from a substituted [1,2,4]triazolo[1,5-c]-pyrimidine-2-sulfonic acid compound and 1-methyl-3-aminoindazole compound or a monofluorinated derivative thereof.

The compounds of the invention include those of Formula I:

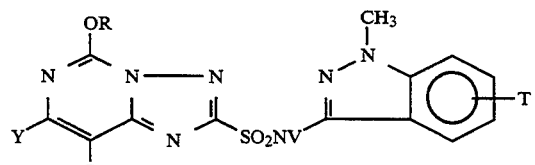

wherein R represents methyl, ethyl, propyl, 1-methylethyl, or cyclopropyl, each optionally monosubstituted with fluorine, chlorine or methoxy, or represents 2,2,2-trifluoromethyl. Methyl and ethyl are typically preferred.

The Y and Z substituents of Formula I are independently selected and include hydrogen, fluoro, chloro, bromo, iodo, methoxy, ethoxy, or methyl which is optionally mono to completely substituted with fluorine. The substituents H, $CH_3$, F, Cl, Br, I, and $OCH_3$ are typically preferred and compounds wherein one of Y and Z represents H, F, Cl, $CH_3$, Br, I, or $OCH_3$ and the other represents H are often more preferred.

The term V in Formula I generally represents hydrogen, CO $(C_1-C_3)$ alkyl optionally singly to completely substituted with fluorine, $CO_2(C_1-C_4)$alkyl, $CO_2(-C_3-C_4)$-alkenyl, $CO_2(C_3-C_4)$alkynyl, $CONH_2$, $CONH(C_1-C_4)$alkyl, or $CON ((C_1-C_4)$alkyl$)_2$. Hydrogen is typically preferred.

Substituent T on the indazole ring of the compounds of Formula I represents hydrogen or fluorine. T is sometimes preferably hydrogen and sometimes preferably fluorine. When T represents fluorine, it is preferably in the 4-position When V represents hydrogen, the compounds of Formula I are acidic and the invention includes the agriculturally acceptable salts.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups singly to completely substituted with fluorine include trifluoro-methyl, monofluoromethyl, 2,2,2-trifluoroethyl, 2,3-difluoropropyl, and the like; trifluoromethyl is often preferred. Typical alkyl groups monosubstituted with methoxy or chloro include 2-chloroethyl, methoxymethyl, and 2-methoxy-1-methylethyl. The term halogen includes fluorine, chlorine, bromine, and iodine.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

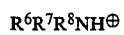

wherein $R^6$, $R^7$, and $R^8$ each, independently represents hydrogen or $(C_1-C_{12})$alkyl, $(C_3-C_{12})$cycloalkyl, or $(C_3-C_{12})$alkenyl, each of which is optionally substituted by one or more hydroxy, $(C_1-C_8)$alkoxy, $(C_1-C_8)$alkylthio or phenyl groups; provided that $R^6$, $R^7$, and $R^8$ are sterically compatible. Additionally, any two of $R^6$, $R^7$, and $R^8$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

A listing of some typical compounds of the invention is given in Table 1. Some of the specifically preferred compounds of the invention include the following: N-(4-fluoro-1-methyl-3-indazolyl)-5,8-dimethoxy[1,2,4]-triazolo[1,5-c]pyrimidine-2-sulfonamide, N-(1-methyl-3-indazolyl)-5-ethoxy-7-fluoro[1,2,4]triazolo[1,5-c]-pyrimidine-2-sulfonamide, N-(4-fluoro-1-methyl-3-indazolyl)5-ethoxy-7-fluoro[1,2,4]triazolo[1,5-c]-pyrimidine-2-sulfonamide, N-(1-methyl-3-indazolyl)-5-methoxy-7-methyl[1,2,4]triazolo[1,5-c]pyrimidine-2-sulfonamide, N-(4-fluoro-1-methyl-3-indazolyl)-5-methoxy-7-methyl[1,2,4]triazolo[1,5-c]pyrimidine-2-sulfonamide, N-(1-methyl-3-indazolyl )-8-chloro-5-methoxy[1,2,4]triazolo[1,5-c]pyrimidine-2-sulfonamide, and N-(4-fluoro-1-methyl-3-indazolyl)-8-chloro-5-methoxy[1,2,4]triazolo[1,5-c]pyrimidine-2-sulfonamide.

TABLE 1

N-INDAZOLYL[1,2,4]TRIAZOLO[1,5-C]PYRIMIDINE-2-SULFONAMIDE COMPOUNDS

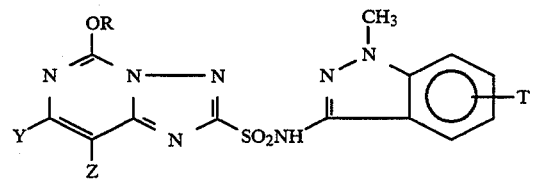

| Cpd. No. | R | Y | Z | T | Form | Melting point, °C. | % C calc. found | % H calc. found | % N calc. found | % S calc. found |
|---|---|---|---|---|---|---|---|---|---|---|
| 1 | C₂H₅ | F | H | H | tan solid | 179–181 | 46.0 / 45.9 | 3.61 / 3.65 | 25.1 / 25.0 | 8.19 / 8.14 |
| 2 | CH₃ | CH₃ | H | H | tan solid | 181–183 | 48.3 / 48.3 | 4.05 / 4.21 | 26.3 / 26.1 | 8.59 / 8.24 |
| 3 | C₂H₅ | F | H | 4-F | tan solid | 203–205 | 44.0 / 44.2 | 3.20 / 3.33 | 24.0 / 23.8 | 7.83 / 7.92 |
| 4 | CH₃ | CH₃ | H | 4-F | tan solid | 181–183 | 46.0 / 46.0 | 3.61 / 3.85 | 25.1 / 24.9 | 8.19 / 8.00 |
| 5 | C₂H₅ | F | H | 6-F | tan solid | 194–196 | 44.0 / 44.0 | 3.20 / 3.43 | 24.0 / 23.8 | 7.83 / 8.12 |
| 6 | CH₃ | CH₃ | H | 6-F | tan solid | 197–198 | 46.0 / 45.9 | 3.61 / 3.82 | 25.1 / 24.8 | 8.19 / 8.24 |
| 7 | C₂H₅ | F | H | 7-F | tan solid | 189–191 | 44.0 / 43.9 | 3.20 / 3.57 | 24.0 / 23.9 | 7.83 / 8.04 |
| 8 | CH₃ | CH₃ | H | 7-F | tan solid | 195–197 | 46.0 / 46.0 | 3.61 / 3.96 | 25.1 / 25.2 | 8.19 / 8.50 |
| 9 | C₂H₅ | F | H | 5-F | tan solid | 198–200 | 44.0 / 44.0 | 3.20 / 3.37 | 24.0 / 23.8 | 7.83 / 7.94 |
| 10 | CH₃ | CH₃ | H | 5-F | tan solid | 208–210 | 36.0 / 45.9 | 3.61 / 3.66 | 25.1 / 24.9 | 8.19 / 8.04 |
| 11 | CH₃ | H | OCH₃ | 4-F | tan solid | 214–216 | 44.2 / 44.0 | 3.46 / 3.62 | 24.1 / 24.0 | 7.87 / 8.13 |
| 12 | CH₃ | H | Cl | 4-F | tan solid | 218–220 | 40.8 / 40.8 | 2.69 / 2.58 | 23.8 / 23.8 | 7.79 / 7.64 |

The compounds of Formula I wherein V represents hydrogen can generally be prepared by combining a 2-chlorosulfonyl[1,2,4]triazolo[1,5-c]pyridine compound of Formula II:

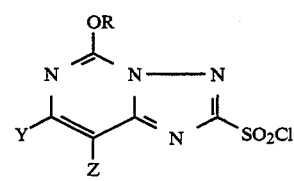

with an appropriately substituted aminoindazole compound of Formula III:

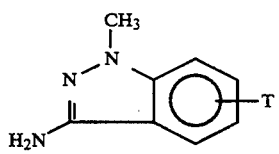

in the presence of pyridine or a methylpyridine compound, and, optionally but preferably, a catalytic amount of dimethyl sulfoxide. The substituents OR, Y, and Z of Formula II and T of Formula III are as defined in hereinbefore.

The preparation is usually accomplished by combining the 2-chlorosulfonyl[1,2,4]triazolo[1,5-c]-pyrimidine compound Formula II, the aminoindazole compound of Formula III, and an inert solvent, such as acetonitrile, N,N-dimethylformamide, N-methyl-2-pyrrolidinone, tetrahydrofuran, and the like, in a vessel and then adding the pyridine or methylpyridine, preferably pyridine, and a catalytic amount of dimethyl sulfoxide. The mixture is allowed to react, typically at ambient temperature, but heating if necessary. After a substantial quantity of the compound of Formula I has formed or a substantial quantity of the chlorosulfonyl compound of Formula II has been consumed, the desired product is recovered, typically=removing the solvent by evaporation, adding water, and removing the liquids from the solid that forms by filtration or centrifugation. The product recovered can be purified, if desired, by extracting with an immiscible organic solvent, such as methylene chloride, and with water. Alternatively, the desired compounds of Formula I can be purified by recrystallization and by other commonly used methods.

Approximately equimolar quantities of the compounds of Formulas I and III are generally used in the preparation of compounds of Formula I although a substantial excess of one or the other may be employed. The pyridine or methylpyridine compound is generally employed in an amount of from at least 1 to about 5 moles per mole of compound of Formula II. Dimethyl sulfoxide is typically used in less than an equimolar amount; amounts over about 0.3 mole per mole of compound of Formula II are usually deleterious. Acetonitrile is often the preferred solvent.

It is sometimes advantageous to prepare the compounds of Formula I by condensing a chlorosulfonyl compound of Formula II with an N-trialkylsilyl derivative of an aminoindazole compound. The method employed is analogous to that described in U.S. Pat. No. 4,910,306 for N-trialkylsilylanilines. The reaction conditions required are essentially the same as those described hereinabove for the condensation of a compound of Formula II with a substituted aminoindazole compound with the exception that the pyridine compound base may be omitted. An aqueous work-up is typically employed. The substituted N-trialkylsilylaminoindazole compounds employed can be prepared from the corresponding substituted aminoindazole compounds by treatment with a trialkylsilyl halide and a trialkylamine as described in U.S. Pat. No. 4,910,306 for aniline compounds. Sodium iodide is typically employed as a catalyst when the halide is chloride. The N-trialkylsilylaminoindazole compounds are typically prepared and used immediately and without purification.

Compounds of Formula I wherein V represents hydrogen can be made from the corresponding compounds related to those of Formula I wherein the moiety OR in the 5-position is replaced by chloro by treatment with an appropriate alkoxide reagent, such as sodium methoxide. Appropriate alkoxide reagents include $(C_1-C_3)$alkoxides optionally monosubstituted with chloro, fluoro or methoxy and 2,2,2-trifluoroethoxide. The reaction is typically carried out in the corresponding alcohol as the solvent. Non-aqueous media are preferred. The reaction conditions employed are similar to those used for the related exchange reactions of 2- and 4-chloropyrimidines. Selective replacement of chlorine in the 5-position can readily be achieved as this chlorine is much more reactive than chlorine in the 7- and 8- positions (Y and/or Z represent Cl).

Compounds of Formula I wherein V represents COR', $C_2R''$, or $CONR'''_2$ can be prepared from compounds of Formula I wherein V represents hydrogen by acylation with a compound of the formula ClCOR', $ClCO_2R''$, or $ClCONR'''_2$, respectively, using conventional procedures known in the art for the acylation of sulfonamides.

The 2-chlorosulfonyl[1,2,4]triazolo[1,5-c]pyrimidine compounds of Formula II and their analogs wherein the moiety OR is replaced by chloro can be prepared by the methods taught in U.S. Pat. No. 5,010,195, incorporated herein by reference.

The preparation of fluoro-N-methyl-3-aminoindazole starting materials is described in the Examples.

While it is possible to utilize the [1,2,4]triazolo[1,5-c]pyrimidine-2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block co-polymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0,001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They can be employed at non-selective (higher) rates of application to control essentially all of the vegetation in an area or, in some cases, at selective (lower) rates of application for the selective control of undesirable vegetation in grass crops, such as corn, wheat, barley, and rice as well as in broadleaf crops, such as soybeans and cotton. While each of the N-indazolyl[1,2,4]-triazolo[1,5-c]pyrimidine-2-sulfonamide compounds encompassed by Formula I is within the scope of the invention, the degree of herbicidal activity, the crop selectivity, and the spectrum of weed control obtained varies depending upon the substituents present.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I post-emergence to relatively immature plants to achieve the maximum control of broadleaf weeds.

Application rates of about 0,001 to about 1 Kg/Ha are generally employed in postemergence operations; for preemergence applications, rates of about 0.01 to about 10 Kg/Ha are generally employed. The higher rates designated generally give non-selective control of a broad variety of undesirable vegetation. The lower rates typically give selective control and, by judicious election, can be employed in the locus of crops.

EXAMPLE

The following Examples are presented to illustrate the various aspects of this invention and should not be construed as limitations to the claims.

1. Preparation of 3-Amino-4-fluoro-1-methylindazole

Methylhydrazine (4.96 g (grams) (108 mmol (millimole)) was added to a solution of 15.0 g (108 mmol) of 2,6-difluorobenzonitrile in 150 mL (milliliters) of ethanol and the mixture was heated to reflux with stirring for 72 hours. The volatiles were then removed by evaporation under reduced pressure and residue was dissolved in dichloromethane. The resulting solution was washed with water, dried over magnesium sulfate, and evaporated to dryness under reduced pressure to obtain the title compound as a white solid. This was recrystallized from ethanol to obtain 10.1 g (57 percent of theory) of the title compound as white crystals melting at 125°–127° C.

Elemental Analysis $C_8H_8FN_3$ Calc.: %C, 58.2; %H, 4.88; %N, 25.4 Found: %C, 58.7; %H, 4.76; %N, 25.9 Nuclear Magnetic Resonance Spectrum (200 MHz (megaHertz), $CDCl_3$): $^1H$: 7.19 (m, 1H), 7.11 (d, 1H, J=8.4), 6.59 (d of d, 1H, J=8.4, 3.3), 5.26 (brs, 2H), 3.72 (s, 3H); $^{13}C$: 157.35, 154.88, 146.20, 146.18, 143.85, 143.76, 127.62, 127.55, 105.31, 105.27, 103.44, 103.24, 101.96, 101.78, 34.74.

3-Amino-5-fluoro-1-methylindazole was prepared analogously from 2,5-difluorobenzonitrile and was obtained in 55 percent yield as a white solid melting at 106°–107° C.

Elemental Analysis $C_8H_8FN_3$ Calc.: %C, 58.2; %H, 4.88; %N, 25.4 Found: %C, 58.0; %H, 5.02; %N, 25.5

3-Amino-6-fluoro-1-methylindazole was prepared analogously from 2,4-difluorobenzonitrile and was obtained in 54 percent yield as a white solid melting at 112°–114° C.

Elemental Analysis $C_8H_8FN_3$ Calc.: %C, 58.2; %H, 4.88; %N, 25.4 Found: %C, 57.9; %H, 4.90; %N, 25.6

3-Amino-7-fluoro-1-methylindazole was prepared analogously from 2,3-difluorobenzonitrile and was obtained in 41 percent yield as a white solid melting at 118°–119° C.

Elemental Analysis $C_8H_8FN_3$ Calc.: %C, 58.2; %H, 4.88; %N, 25.4 Found: %C, 58.6; %H, 4.55; %N, 25.5

2. Preparation of N-(1-Methyl-3-indazolyl)-5-methoxy-7-methyl[1,2,4]triazolo[1,5-c]pyrimidine-2-sulfonamide Pyridine (0.30 g, 3.8 mmol) and dimethyl sulfoxide (DMSO) (0.030 g, 0.38 mmol) were added with stirring to a solution of 1.0 g (3.8 mmol) 2-chlorosulfonyl-5-methoxy-7-methyl[1,2,4]triazolo[1,5c]-pyrimidine and 0.56 g (3.8 mmol) of 3-amino-1-methylindazole in 15 mL of acetonitrile and the mixture was allowed to react at ambient temperature for 18 hours. The volatiles were then removed by evaporation under reduced pressure and the residue was taken up in dichloromethane. The resulting mixture was washed with water. The solids present were then collected by filtration, washed with 20 mL of ether, and resuspended in 50 mL of water. The solids were collected by filtration, washed with ether, and dried at 40° C. under reduced pressure to obtain 0.961 g (68 percent of theory) of the title compound as a tan solid melting at 181°–183° C.

Elemental Analysis $C_{15}H_{15}FN_7O_3S$ Calc.: %C, 48.3; %H, 4.05; %N, 26.3; %S, 8.59 Found: %C, 48.3; %H, 4.21; %N, 26.1; %S, 8.24 Nuclear Magnetic Resonance Spectrum (200 MHz, DMSO-d6): $^1H$: 11.38 (brs, 1H), 7.62 (d, 1H, J=2.1), 7.53 (d, 1H, J=2.1), 7.38 (s, 1H), 7.35 (m, 1H), 7.07 (m, 1H), 4.17 (s, 3H), 3.85 (s, 3H), 2.48 (s, 3H); $^{13}C$: 164.3, 156.2, 155.2, 148.3, 140.5, 135.7, 126.6, 120.4, 119.9, 117.9, 109.7, 103.0, 56.5, 35.2, 23.5.

3. Preparation of N-(4-Fluoro-1-methyl-3-indazolyl)-5-ethoxy-7-fluoro[1,2,4]triazolo[1,5c]pyrimidine-2-sulfonamide Pyridine (0.48 g, 6.1 mmol) and dimethyl sulfoxide (0.048 g, 0.61 mmol) were added with stirring to a solution of 1.7 g (6.1 mmol) 2-chlorosulfonyl-5-ethoxy-7-fluoro[1,2,4]triazolo[1,5-c]pyrimidine and 1.00 g (6.1 mmol) of 3-amino-4-fluoro-1-methylindazole in 15 mL of acetonitrile and the mixture was allowed to react at ambient temperature for 18 hours. The volatiles were then removed by evaporation under reduced pressure and the residue was taken up in dichloromethane. The resulting mixture was washed with water. The solids present were then collected by filtration, washed with 20 mL of ether, and resuspended in 50 mL of water. The solids were collected by filtration, washed with ether, and dried at 40° C. under reduced pressure to obtain 0.57 g (23 percent of theory) of the title compound as a tan solid melting at 203°–205° C.

Elemental Analysis $C_{15}H_{13}F_2N_7O_3S$ Calc.: %C, 44.0; %H, 3.20; %N, 24.0; %S, 7.83 Found: %C, 44.2; %H, 3.33; %N, 23.8; %S, 7.92 Nuclear Magnetic Resonance Spectrum (200 MHz, DMSO-d6): $^1H$: 11.28 (brs, 1H), 7.44 (s, 1H), 7.42 (m, 1H), 7.37 (m, 1H) 6.84 (d of d, 1H, J=8.4, 3.3), 4.68 (q, 2H, J=7.0) 3.89 (s, 3H), 1.44 (t, 3H J=7.0); $^{13}C$: 175.3, 165.5, 163.1, 160.7, 157.1, 156.9, 1551.7, 153.1, 149.2, 148.9, 143.3, 143.2, 138.7, 132.8, 127.8, 127.7, 109.4, 109.1, 106.6, 105.5, 105.3, 86.8, 86.4, 65.5, 35.8, 13.8.

4. Evaluation of Postemergence Herbicidal Activity

Seeds of the desired test plant species were planted in Grace-Sierra MetroMix ® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

TABLE 2

| | | | POSTEMERGENCE HERBICIDAL ACTIVITY | | | | | | | | | |
|---|---|---|---|---|---|---|---|---|---|---|---|---|
| Cpd. No. | Rate, ppm | Cockle-bur | Jimson-weed | Lambs-quarter | Morning-glory | Velvet-leaf | Veron-ica | Wild Buckwheat | Black-grass | Barnyard grass | Johnson-grass | Wild oat |
| 1 | 62.5 | 80 | — | 98 | 75 | 98 | 90 | 80 | 90 | 95 | 80 | 99 |
| 2 | 31.3 | 95 | — | 95 | 80 | 98 | 100 | 80 | 80 | 78 | 80 | 80 |
| 3 | 31.3 | 20 | 50 | 65 | 100 | 100 | 90 | 80 | 80 | 75 | 75 | 98 |
| 4 | 62.5 | 80 | — | 75 | 75 | 75 | 100 | 85 | 60 | 25 | 70 | 85 |

TABLE 2-continued

| | | POSTEMERGENCE HERBICIDAL ACTIVITY | | | | | | | | | | |
|---|---|---|---|---|---|---|---|---|---|---|---|---|
| Cpd. No. | Rate, ppm | Cockle-bur | Jimson-weed | Lambs-quarter | Morning-glory | Velvet-leaf | Veron-ica | Wild Buckwheat | Black-grass | Barnyard grass | Johnson-grass | Wild oat |
| 5 | 500 | 75 | 50 | 80 | 50 | 85 | 100 | 100 | 100 | 75 | 75 | 95 |
| 6 | 125 | 100 | 80 | 85 | 75 | 85 | 100 | 80 | 85 | 75 | 80 | 98 |
| 8 | 2000 | 65 | 60 | 70 | 0 | 20 | 80 | 0 | 50 | 0 | 0 | 35 |
| 9 | 125 | 80 | 65 | 75 | 88 | 90 | 80 | 88 | 88 | 80 | 88 | 85 |
| 10 | 31.5 | 80 | 45 | 80 | 45 | 97 | 100 | 100 | 70 | 0 | 75 | 99 |
| 11 | 31.5 | 80 | 55 | 80 | 85 | 80 | 90 | 85 | 40 | 70 | 95 | 85 |
| 12 | 3.9 | — | 90 | 50 | 85 | 88 | 88 | 75 | 0 | 50 | 78 | 45 |

5. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween ® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°-29° C. during the day and 22°-28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

| | | PREEMERGENCE HERBICIDAL ACTIVITY | | | | | | |
|---|---|---|---|---|---|---|---|---|
| Cpd. No. | Rate, Kg/Ha | Morning-glory | Pigweed | Velvet-leaf | Wild wheat | Black-grass | Barnyard Grass | Giant foxtail | Johnson-grass |
| 1 | 0.56 | 40 | 100 | 90 | 80 | 98 | 95 | 75 | — |
| 2 | 0.56 | 70 | 100 | 85 | 80 | 95 | 95 | 80 | — |
| 3 | 0.28 | 80 | 98 | 80 | 85 | 95 | 80 | 50 | 98 |
| 5 | 0.28 | 60 | 98 | 65 | 80 | 85 | 98 | 60 | 80 |
| 6 | 0.56 | 30 | 100 | 80 | 75 | 85 | 80 | 50 | 95 |
| 9 | 0.28 | 30 | 75 | 40 | 70 | 85 | 85 | 50 | 80 |
| 10 | 0.28 | 10 | 85 | 30 | 60 | 30 | 25 | 25 | 85 |
| 11 | 0.14 | 60 | 100 | 60 | 70 | 70 | 60 | 50 | 80 |
| 12 | 0.07 | 80 | 98 | 90 | 95 | 40 | 75 | 70 | 95 |

What is claimed is:

1. An N-indazolyl[1,2,4]triazolo[1,5-c]pyrimidine-2-sulfonamide compound of the formula:

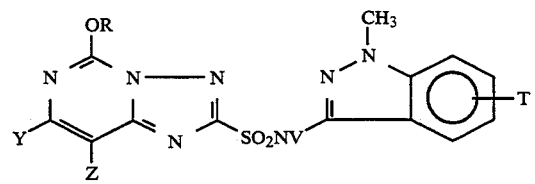

wherein.

R represents $CH_2CF_3$ or $(C_1-C_3)$alkyl optionally monosubstituted with F, Cl, or $OCH_3$;

Y and Z, each independently represents H, F, Cl, Br, I, $OCH_3$, $OC_2H_5$, or $CH_3$ optionally mono to completely substituted with F;

T represents H or F

V represents H, COR', $CO_2R''$, or $CONR'''_2$;

R' represents $(C_1-C_3)$alkyl optionally singly to completely substituted with fluorine;

R" represents $(C_1-C_4)$alkyl, $(C_3-C_4)$alkenyl, or $(C_3-C_4)$alkynyl,

R''' represents H or $(C_1-C_4)$alkyl; and when v represents H, the agriculturally acceptable salts thereof.

2. A compound according to claim 1 wherein V represents H.

3. A compound according to claim 1 wherein R represents methyl or ethyl.

4. A compound according to claim 1 wherein one of Y and Z represents H, $CH_3$, F, Cl, Br, I, or $OCH_3$, and the other represents H.

5. A compound according to claim 1 wherein T represents 4-F.

6. A compound according to claim 5 selected from N-(4-fluoro-1-methyl-3-indazolyl)-5,8-dimethoxy[1,2,4]triazolo[1,5-c]pyrimidine-2-sulfonamide, N-(4-fluoro-1-methyl-3-indazolyl)-5-ethoxy-7-fluoro[1,2,4]-triazolo-[1,5-c]pyrimidine-2-sulfonamide, N-(4-fluoro-1-methyl-3-indazolyl)-5-methoxy-7-methyl[1,2,4]-triazolo[1,5-c]pyrimidine-2-sulfonamide, and N-(4-fluoro-1-methyl-3-indazolyl)-8-chloro-5-methoxy[1,2,4]triazolo[1,5-c]pyrimidine-2-sulfonamide.

7. An herbicidal composition comprising an herbicidally effective amount of an N-indazolyl[1,2,4]-triazolo[1,5-c]pyrimidine-2-sulfonamide compound of the formula:

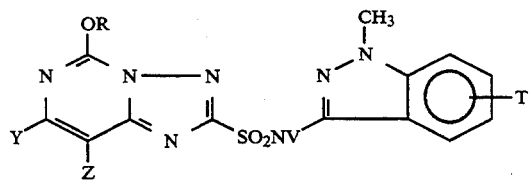

wherein
R represents $CH_2CF_3$ or $(C_1-C_3)$alkyl optionally monosubstituted with F, Cl, or $OCH_3$;
Y and Z, each independently represents H, F, Cl, Br, I, $OCH_3$, $OC_2H_5$, or $CH_3$ optionally mono to completely substituted with F;
T represents H or F
V represents H, COR', $CO_2R''$, or $CONR'''_2$;
R' represents $(C_1-C_3)$alkyl optionally singly to completely substituted with fluorine;
R'' represents $(C_1-C_4)$alkyl, $(C_3-C_4)$alkenyl, or $(C_3-C_4)$alkynyl,
R''' represents H or $(C_1-C_4)$alkyl; and when V represents H, the agriculturally acceptable salts thereof in admixture with an agriculturally acceptable adjuvant or carrier.

8. A composition according to claim 7 wherein V represents H.

9. A composition according to claim 7 wherein R represents methyl or ethyl.

10. A composition according to claim 7 wherein one of Y and z represents H, $CH_3$, F, Cl, Br, I, or $OCH_3$, and the other represents H.

11. A composition according to claim 7 wherein T represents 4-F.

12. A composition according to claim 11 wherein the compound is selected from N-(4-fluoro-1-methyl-3-indazolyl)-5,8-dimethoxy[1,2,4]triazolo[1,5-c]pyrimidine-2-sulfonamide, N-(4-fluoro-1-methyl-3-indazolyl)-5-ethoxy-7-fluoro[1,2,4]triazolo[1,5-c]pyrimidine-2-sulfonamide, N-(4-fluoro-1-methyl-3-indazolyl)-5-methoxy-7-methyl[1,2,4]triazolo[1,5-c]pyrimidine-2-sulfonamide, and N-(4-fluoro-1-methyl-3-indazolyl)-8-chloro-5-methoxy[1,2,4]triazolo[1,5-c]pyrimidine-2-sulfonamide.

13. A method of controlling undesirable vegetation which comprises applying to said vegetation or to the locus thereof an herbicidally effective amount of an N-indazolyl[1,2,4]triazolo[1,5-c]pyrimidine-2-sulfonamide compound of the formula:

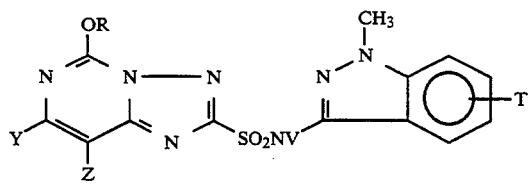

wherein
R represents $CH_2CF_3$ or $(C_1-CF_3)$alkyl optionally monosubstituted with F, Cl, or $OCH_3$;
Y and Z, each independently represents H, F, Cl, Br, I, $OCH_3$, $OC_2H_5$, or $CH_3$ optionally mono to completely substituted with F;
T represents H or F;
V represents H, COR', $CO_2R''$, or $CONR'''_2$;
R' represents $(C_1-C_3)$alkyl optionally singly to completely substituted with fluorine; R'' represents $(C_1-C_4)$alkyl, $(C_3-C_4)$alkenyl, or $(C_3-C_4)$ alkynyl,
R''' represents H or $(C_1-C_4)$alkyl; and when V represents H, the agriculturally acceptable salts thereof.

14. A method according to claim 13 wherein V represents H.

15. A method according to claim 13 wherein R represents methyl or ethyl.

16. A method according to claim 13 wherein one of Y and Z represents H, $CH_3$, F, Cl, Br, I, or $OCH_3$ and the other represents H.

17. A method according to claim 17 wherein T represents 4-F.

18. A method according to claim wherein the compound is selected from N-(4-fluoro-1-methyl-3-indazolyl)-5,8-dimethoxy[1,2,4]triazolo[1,5-c]pyrimidine-2-sulfonamide, N-(4-fluoro-1-methyl-3-indazolyl)-5-ethoxy-7-fluoro[1,2,4 ]triazolo[1,5-c]pyrimidine-2-sulfonamide, N-(4-fluoro-1-methyl-3-indazolyl)-5-methoxy-7-methyl[1,2,4]triazolo[1,5-c]pyrimidine-2-sulfonamide, and N-(4-fluoro-1-methyl-3-indazolyl)-8-chloro-5-methoxy[1,2,4]triazolo[1,5-c]pyrimidine-2-sulfonamide.

19. The method according to claim 13 wherein the compound is applied postemergently.

20. A 3-aminoindazole compound of the formula:

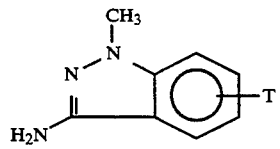

wherein T represents F.

21. The compound according to claim 20 which is 3-amino-4-fluoro-1-methylindazole.

* * * * *